(12) United States Patent
Miller et al.

(10) Patent No.: US 11,154,419 B2
(45) Date of Patent: Oct. 26, 2021

(54) SIMULTANEOUS THERMAL AND COOLING THERAPEUTIC DEVICE

(71) Applicants: Bruce Wayne Miller, Naples, FL (US); Wayne Allan Miller, Land O Lakes, FL (US)

(72) Inventors: Bruce Wayne Miller, Naples, FL (US); Wayne Allan Miller, Land O Lakes, FL (US)

(*) Notice: Subject to any disclaimer, the term of this patent is extended or adjusted under 35 U.S.C. 154(b) by 0 days.

(21) Appl. No.: 17/192,948

(22) Filed: Mar. 5, 2021

(65) Prior Publication Data
US 2021/0186750 A1 Jun. 24, 2021

Related U.S. Application Data

(63) Continuation-in-part of application No. 16/244,498, filed on Jan. 10, 2019, now abandoned.

(60) Provisional application No. 62/691,455, filed on Jun. 28, 2018.

(51) Int. Cl.
*A61F 7/08* (2006.01)
*A61F 7/10* (2006.01)
*A61F 7/02* (2006.01)

(52) U.S. Cl.
CPC .................. *A61F 7/08* (2013.01); *A61F 7/02* (2013.01); *A61F 7/10* (2013.01); *A61F 2007/023* (2013.01); *A61F 2007/0215* (2013.01); *A61F 2007/0217* (2013.01); *A61F 2007/0219* (2013.01); *A61F 2007/0231* (2013.01); *A61F 2007/0242* (2013.01); *A61F 2007/0244* (2013.01); *A61F 2007/0261* (2013.01); *A61F 2007/0263* (2013.01); *A61F 2007/0268* (2013.01); *A61F 2007/0269* (2013.01); *A61F 2007/0279* (2013.01); *A61F 2007/0298* (2013.01); *A61F 2007/108* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,367,731 A | * | 11/1994 | O'Sullivan | .......... A47G 9/0253 5/645 |
| 6,475,535 B1 | * | 11/2002 | Mizushima | ........ A61K 36/9068 424/40 |
| 2012/0065259 A1 | * | 3/2012 | Zhang | .................. A61K 31/245 514/537 |
| 2014/0188199 A1 | * | 7/2014 | Enderby | .................... A61F 7/08 607/108 |
| 2015/0351956 A1 | * | 12/2015 | Enderby | .................... A61F 7/08 607/108 |
| 2017/0360602 A1 | * | 12/2017 | Nishioka | ................. A61F 7/034 |

* cited by examiner

*Primary Examiner* — Joseph A Stoklosa
*Assistant Examiner* — Adam J Avigan
(74) *Attorney, Agent, or Firm* — Tiffany C. Miller; Inventions International Inc.

(57) ABSTRACT

A therapeutic device combines both hot and cold therapy to work simultaneously together. The therapeutic device has a first portion being made of a material capable of being heated to a first temperature and a second portion having a fastener capable of connecting to a cold pack having a second temperature. The application of both hot and cold to the site of an injury of a user stimulates blood circulation to an injured muscle with heat and reduces inflammation with cold to facilitate a faster and more efficient recovery process of the afflicted area.

16 Claims, 7 Drawing Sheets

SIMULTANEOUS THERMAL AND COOLING THERAPEUTIC DEVICE

CROSS REFERENCE TO RELATED APPLICATIONS

This application is a U.S. Continuation-In-Part Utility Patent Application entitled, "Simultaneous Thermal and Cooling Therapeutic Device", claiming priority to co-pending U.S. Non-Provisional Utility patent application Ser. No. 16/244,498, filed Jan. 10, 2019, entitled, "Simultaneous Thermal and Cooling Therapeutic Device", which claims priority to U.S. Provisional Patent Application No. 62/691,455, filed June. 28, 2018, entitled, "HC Therapy".

BACKGROUND OF THE INVENTION

1. Field of the Invention

This invention relates, generally, to a simultaneous thermal and cooling therapeutic device. More particularly, it relates to a thermal apparatus having a removable cold pack.

2. Background Art

This novel therapeutic device is configured to help injuries associated with including, but not limited to, sore muscles, sprained muscles, or pulled muscles. The therapeutic device when applied to the injury reduces inflammation with ice or cold packs while also stimulating circulation in the area with hot packs, simultaneously. Many therapeutic devices in today's market either use hot or cold to help with symptoms associated with injury. However, these therapeutic devices do not use both hot and cold at the same time. Using hot and cold together can result in a faster and more efficient way to reduce inflammation, therefore reducing the amount of therapy or product needed to alleviate the pain of the area. Thus, there is a need for a therapeutic device that combines the use of hot and cold in a single therapeutic device in an attempt to save time and energy, to provide more comfort to a user, and to more effectively reduce injury mediated inflammation.

Currently, when an individual has a muscle injury, they use either ice alone or heat alone to treat it. In an example of a muscle injury treatment method, contrast therapy is the application of heat for approximately 20 minutes followed by an application of cold such as a cold pack or ice for approximately 20 minutes. There is a need for a novel therapeutic device configured to combine a cold and hot pack together to deliver simultaneous hot and cold therapy to a user. As a result, the novel therapeutic device is configured to reduce inflammation and stimulate more blood flow to the injured or swollen area. The sensation a user experiences from using a combined hot and cold therapeutic device relaxes the nerves associated with the brain's response to injury. For example, by using hot and cold at the same time, the signals of the brain become confused and may alleviate the area of injury quicker.

In another example of a muscle injury treatment method, cold therapy is effective for pain and inflammation reduction. Cold cools the skin tissue which results in narrowing of blood vessels in a process vasoconstriction. Vasoconstriction reduces swelling, reduces inflammation, and reduces muscle spasms of the injured area. There is a need to take a standard cold pack and combine it together with a hot pack, resulting in a contrast therapy that works at the same time.

In another example of a muscle injury treatment method, heat therapy effectively increases tissue extensibility and improves muscle movement after an injury. Heat therapy also induces vasodilation which draws blood into targeted tissues and increases blood flow. This increase in blood flow is beneficial because the blood flow delivers required oxygen and nutrients to the injured area as well as removes cellular waste. The warmth of heat therapy is associated with a decrease in muscle spasms, relaxes tense muscles, relieves pain, and may increase the range in motion. Heat therapy also stimulates the sensory receptors in the skin, resulting in a decrease in transmission of pain signals to the brain in an attempt to relieve discomfort during an injury. Thus, heat therapy promotes healing of the muscles and joints. There is a need to take a standard hot pack and combine it together with a cold pack, resulting in a contrast therapy that works at the same time.

However, in view of the prior art considered as a whole at the time the present invention was made, it was not obvious to those of ordinary skill in the pertinent art how the identified needs could be fulfilled.

SUMMARY OF THE INVENTION

The long-standing but heretofore unfulfilled need for a therapeutic device configured to combine both hot and cold therapy to work simultaneously together. The therapeutic device has a first portion being made of a material capable of being heated to a first temperature and a second portion having a fastener capable of connecting to a cold pack having a second temperature. The application of both hot and cold to the site of an injury of a user stimulates blood circulation to an injured muscle with heat and reduces inflammation with cold to facilitate a faster and more efficient recovery process of the afflicted area, and is now met by a new, useful, and non-obvious invention.

The following description and drawings are illustrative and are not to be construed as limiting. Numerous specific details are described to provide a thorough understanding. However, in certain instances, well known or conventional details are not described in order to avoid obscuring the description. References to one or an embodiment in the present disclosure are not necessarily references to the same embodiment; and, such references refer to at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

In an alternate embodiment, the standard hot packs and cold packs can be combined together with a fastener, including, but not limited to, hook and loop attachments, a slit of fabric, a plastic pocket, or a magnet.

In a preferred embodiment, a therapeutic device is shaped like a large donut sized pack. The outer part of the pack will be for heat that is configured to be heated by a user in a microwave. The inner part will have at least a portion of a piece of hook and loop attachments sewn, a slit of fabric or a magnet that is configured for a user to place a cold pack into the center and stay secured. This therapeutic device can then be placed on the injury and both the heat and cold will work together to stimulate blood flow and reduce inflammation to the afflicted area.

It is within the scope of this invention for the novel therapeutic device to have any shape and size including, but not limited to, a donut shape, rounded, oval, square, or rectangular. The novel therapeutic device operates with one portion being hot and another portion having a fastener, including, but not limited to, hook and loop attachments, a slit of fabric, a plastic pocket, or a magnet configured to receive a cold pack.

In an alternate embodiment, the novel therapeutic device is a shape including, but not limited to, a square or a rectangular shape having a plurality of pockets connected thereto. For example, the therapeutic device can have four different slots each positioned in a horizontal orientation. Each of the four different slots are configured to receive four hot and cold packs alternately positioned.

The novel simultaneous thermal and cooling therapeutic device is a donut shape having an outer perimeter edge. The outer perimeter edge is a first pack capable of being heated to a first temperature. The therapeutic device can be heated in a microwave, which would warm the outer perimeter edge portion to a warm or hot first temperature. The therapeutic device has a substantially central portion that does not have a portion of a first pack and does not have a heated temperature. The substantially central portion of the therapeutic device is configured to receive a removable second pack capable of being cooled to a second temperature. The first temperature of the first pack is of a different temperature than the second temperature of said second pack.

It is within the scope of this invention for the therapeutic device to have an outer perimeter edge being a first pack capable of being cooled to first temperature. Additionally, it is also within the scope of this invention for the substantially central portion of the therapeutic device to be configured to receive a removable second pack capable of being heated to a second temperature.

In another embodiment, the simultaneous thermal and cooling therapeutic device has an outer perimeter edge being a first pack made of a thermally conductive material or being made of any material capable of retaining a thermally conductive material. The thermally conductive material includes, but is not limited to, microwavable beads, rice, rice beads, or any material that can be safely heated up in a microwave. In an example, the outer perimeter edge of the therapeutic device is a fabric material having a pocket retaining rice. In another example, the outer perimeter edge of the therapeutic device is a plastic material having a pocket retaining a gel that is capable of being heated. In yet another example, the outer perimeter edge of the therapeutic device is a first pack being a vessel retaining water. In yet another example, the outer perimeter edge of the therapeutic device is a first pack being a vessel retaining a thermally conductive gel. In yet another example, the outer perimeter edge of the therapeutic device is a first pack being a vessel retaining a liquid. In yet another example, the outer perimeter edge of the therapeutic device is a first pack being a hot pack.

In another embodiment, the simultaneous thermal and cooling therapeutic device has a first donut shaped pack configured to be heated to a first temperature.

In another embodiment, the simultaneous thermal and cooling therapeutic device has a middle portion of the donut shaped hot pack capable of receiving a removable second pack. The removable second pack is configured to be cooled to a second temperature. It is within the scope of this invention for the removable second pack to be a vessel retaining including, but not limited to, a refrigerant gel, ice, freezable gel, water, or beads. The vessel is a container, a pouch, a pack capable of retaining the material to be cooled to the second cooler temperature. It is also within the scope of this invention for the cold pack to be made from a flexible soft plastic material on the outside that retains the substance or material configured to be cooled to a second temperature.

The material that would hold the packs can be a cotton material that is cut, shaped, and filled with the beads, then sewn in to fit the shape or pattern. The hot pack and cold pack will be separate components of the therapeutic device. After the therapeutic device having the hot pack is heated and the cold pack is cooled, the cold pack can be removably connected to the central portion of the therapeutic device. The therapeutic device can then be applied to the injured area and provide simultaneous hot and cold therapy to a user.

In another embodiment, the simultaneous thermal and cooling therapeutic device has a substantially central portion having a pocket. The pocket is configured to retain the removable second pack.

In another embodiment, the simultaneous thermal and cooling therapeutic device has a substantially central portion having a first portion of a fastener. The removable second pack has a second portion of a fastener. The first portion of the fastener removably connects to the second portion of said fastener. In an example, the first portion of a fastener is the hook portion and the second portion of a fastener is the loop portion. The hook portion mates with the loop portion to form an attachment. It is within the scope of this invention for the fastener to be an adhesive, a button, a clip, or a magnet. This allows for the cold pack to connect to the central portion of the therapeutic device, thereby, orienting the hot pack to be on the outer perimeter edge of the therapeutic device and the cold pack located in the center of the therapeutic device.

In another embodiment, the simultaneous thermal and cooling therapeutic device has a substantially central portion having a length of material. The length of material has a first end located opposite a second end. The first end of the length of material and said second end of the length of material are connected to the therapeutic device. The length of material can be an elastic material capable of stretching to retain a plurality of sexed cold packs. The length of material is configured to retain a removable second pack when the removable second pack is inserted under the length of material.

In yet another embodiment, the simultaneous thermal and cooling therapeutic device has an outer perimeter edge being a hot pack. The hot pack is made of a thermally conductive material capable of being heated to a first temperature. The therapeutic device has a substantially central portion configured to receive a removable cold pack. The removable cold pack is made of a material capable of being cooled to a second temperature. The second temperature of the removable cold pack is a lower temperature than the first temperature of the hot pack. The removable cold pack is connected to the substantially central portion of the therapeutic device.

The substantially central portion of the therapeutic device can have a pocket configured to retain the removable cold pack. In another embodiment, the substantially central portion of the therapeutic device can have a first portion of a fastener. The removable cold pack has a second portion of a fastener. The first portion of the fastener removably connects to the second portion of the fastener. It is within the scope of this invention for the second portion of the fastener to be the outer surface of the cold pack. In another embodiment, the substantially central portion of the therapeutic device has a length of material having a first end located opposite a second end. The first end of the length of material and the second end of the length of material are connected to the central portion of the therapeutic device. The length of material is configured to retain the removable cold pack when the removable cold pack is inserted under the length of material.

It is within the scope of this current invention for the removable cold pack to be reusable or an instant cold pack.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
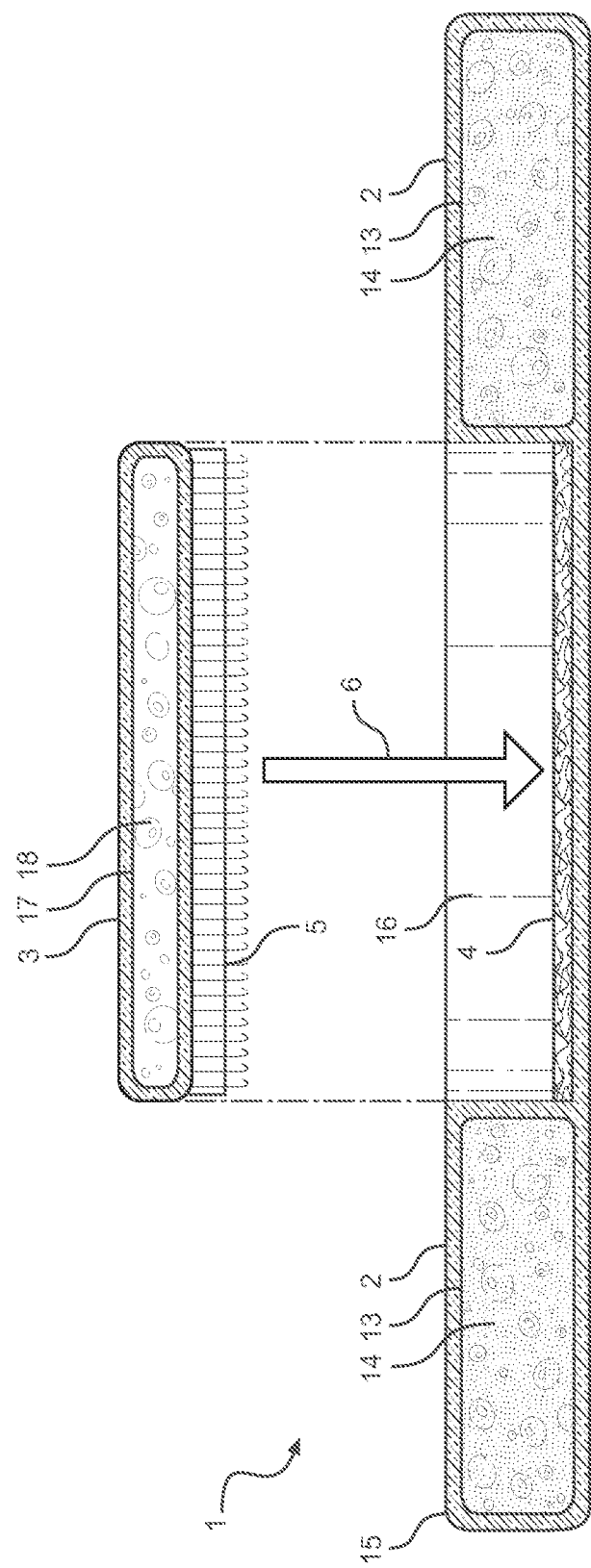
FIG. 1 is a side cut-away view of the novel therapeutic device having an outer perimeter edge having a compartment retaining a thermally conductive material and a substantially central portion having a first portion of a fastener receiving a removable cold pack having a second portion of a fastener connected thereto.

FIG. 1 illustrates novel therapeutic device 1 having hot pack 2 located on an outer perimeter edge 15 of therapeutic device 1. Hot pack 2 has compartment 13 retaining thermally conductive material 14. Therapeutic device 1 has central portion 16 forming a chamber or a recess capable of receiving 6 (FIGS. 1 and 3) removable cold pack 3. Removable cold pack 3 has compartment 17 capable of retaining refrigerant gel 18. Central portion 16 of therapeutic device 1 has first portion of fastener 4 connected to at least one inner wall surface or bottom surface of central portion 16. The first portion of fastener 4 featured in FIG. 1 are the loops of a hook and loop fastening mechanism. Removable cold pack 3 has at least a portion of a fastener 5 connected thereto. In particular, second portion of fastener 5 is the hook portion of a hook and loop fastener mechanism. Second portion of fastener 5 of removable cold pack 3 is configured to connect to 6 first portion of fastener 4 of central portion 16 of therapeutic device 1.

Figure 3:
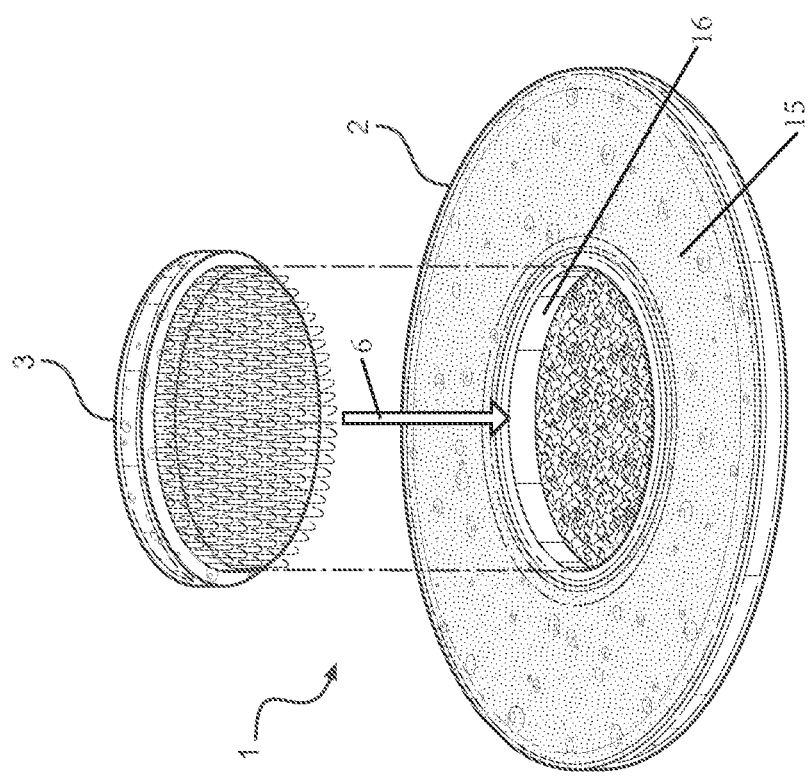
FIG. 3 is an exploded view of the novel therapeutic device having an outer perimeter edge being a hot pack and a substantially central portion being a removable cold pack.
Figure 2:
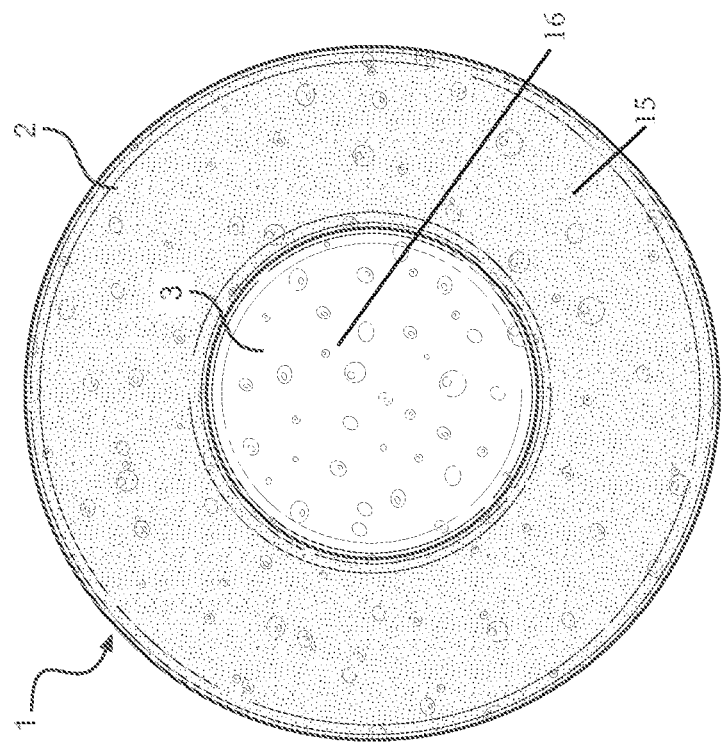
FIG. 2 is a top perspective view of the novel therapeutic device having an outer perimeter edge being a hot pack and a substantially central portion being a removable cold pack.

FIGS. 2-3 illustrate therapeutic deice 1 having hot pack 2 located on outer perimeter edge 15 of therapeutic device 1 and removable cold pack 3 located on central portion 16 of therapeutic device 1. FIGS. 2-3 illustrate different views of FIG. 1. Although not shown, it is within the scope of this invention for the cold pack to be located on an outer perimeter edge of the therapeutic device and a removable hot pack located on a central portion of the therapeutic device.

Figure 4:
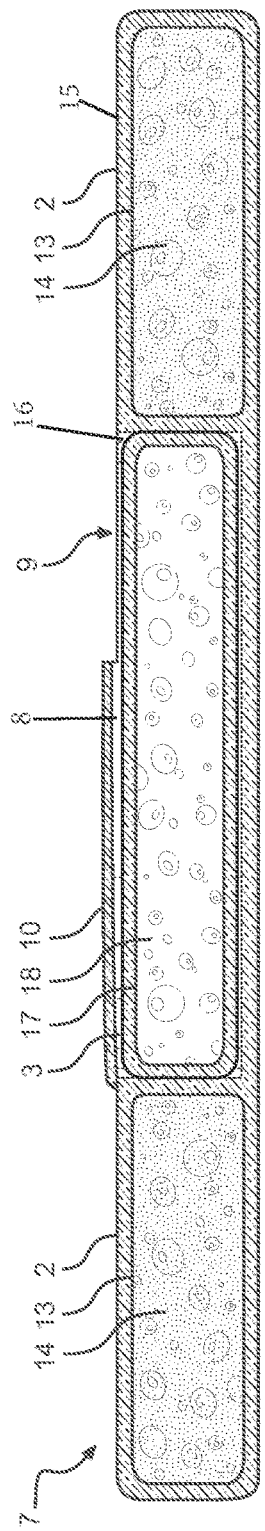
FIG. 4 is a side cut-away view of an alternate embodiment of the novel therapeutic device having an outer perimeter edge having a compartment retaining a thermally conductive material and a substantially central portion forming a pocket with a length of material receiving a removable cold pack.
Figure 5:
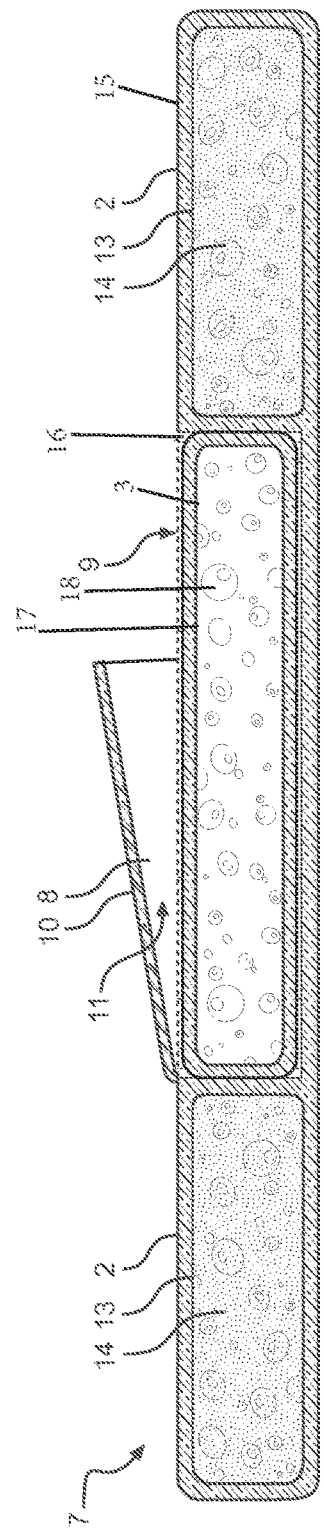
FIG. 5 is a side cut-away view of an alternate embodiment of the novel therapeutic device having an outer perimeter edge having a compartment retaining a thermally conductive material and a substantially central portion forming a pocket with a length of material being expanded to receive a removable cold pack.

FIGS. 4-5 depict an alternate embodiment of therapeutic device 7 in which the fastener connecting the removable cold pack 3 to therapeutic device 1 is a length of material 10 partially overlaying at least a portion of pocket 8. Pocket 8 is located at central portion 16 of therapeutic device 7. Pocket 8 has pocket opening 9. In this embodiment, opening 9 is located on an edge of central portion 16. It is within the scope of this invention for removable cold pack 3 having a compartment 17 retaining refrigerant gel 18. Therapeutic device 7 has hot pack 2 located on an outer perimeter edge 15 of therapeutic device 7. Hot pack 2 has compartment 13 retaining thermally conductive material 14. FIG. 4 illustrates length of material 10 in a closed orientation being made of any material including, but not limited to, a stretchy material capable of retaining removable cold pack 3 within pocket 8. FIG. 5 illustrates length of material 10 being oriented in an open configuration 11 to allow for more clearance for removable cold pack 3 to slide into pocket 8. A user may grasp length of material 10 and peel it or pull it to create a larger opening 9 of pocket 8. For example, a user (not shown) may grasp at least a portion of length of material 10 and pull the length of material 10 away from central portion 16 to create a larger opening 9 for removable cold pack 3 to be inserted into pocket 8.

Figure 6:
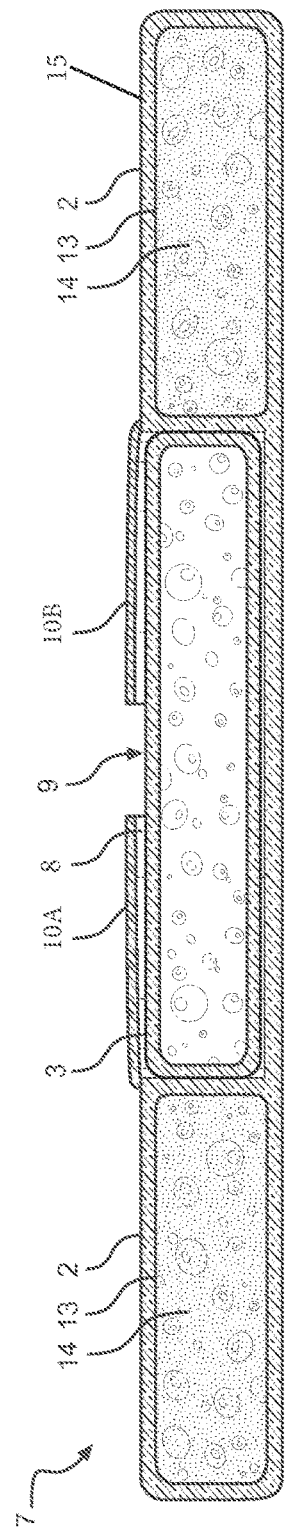
FIG. 6 is a side cut-away view of another alternate embodiment of the novel therapeutic device having an outer perimeter edge having a compartment retaining a thermally conductive material and a substantially central portion forming a pocket with a length of material receiving a removable cold pack.
Figure 7:
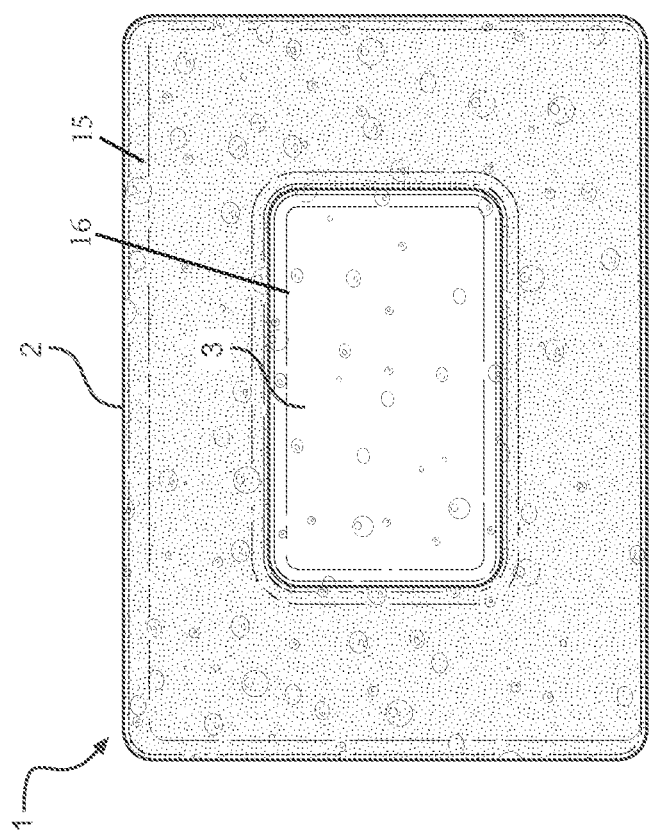
FIG. 7 is a top view of another alternate embodiment of the novel therapeutic device having an outer perimeter edge having a compartment retaining a thermally conductive material and a substantially central portion forming a pocket with a length of material receiving a removable cold pack.

FIGS. 6-7 illustrate an alternate embodiment of therapeutic device 7 in which the fastener holding removable cold pack 3 within pocket 8 (FIG. 6) is a length of material 10A and 10B overlaying at least a portion of pocket 8 (FIG. 6). Removable cold pack 3 is inserted into pocket 8 through opening 9. In this embodiment, opening 9 is located at a central portion of central portion 16 between length of material 10A and 10B. Therapeutic device 7 has outer perimeter edge 15 being hot pack 2. FIG. 6 shows hot pack 2 having compartment 13 retaining thermally conductive material 14. It is within the scope of the therapeutic device 7 to have substantially central portion 16 having a first portion of a fastener being a magnet. Removable second pack can have a second portion of a fastener being another magnet. The first portion of the magnet removably connects to second portion of fastener being a magnet (not shown).

Figure 8:
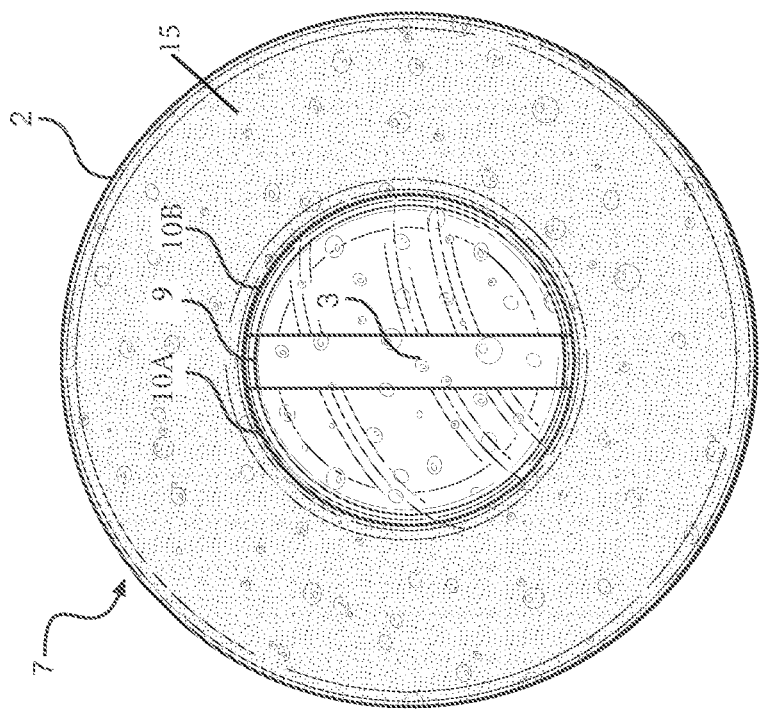
FIG. 8 is a top perspective view of an alternate embodiment of the novel therapeutic device having a square shape and having an outer perimeter edge being a hot pack and a substantially central portion being a removable cold pack.

FIG. 8 shows an alternate embodiment of the novel therapeutic device 1 in FIGS. 1-3 having a square shape and having an outer perimeter edge 15 being hot pack 2 and substantially central portion 16 being removable cold pack 3.

Figure 9:
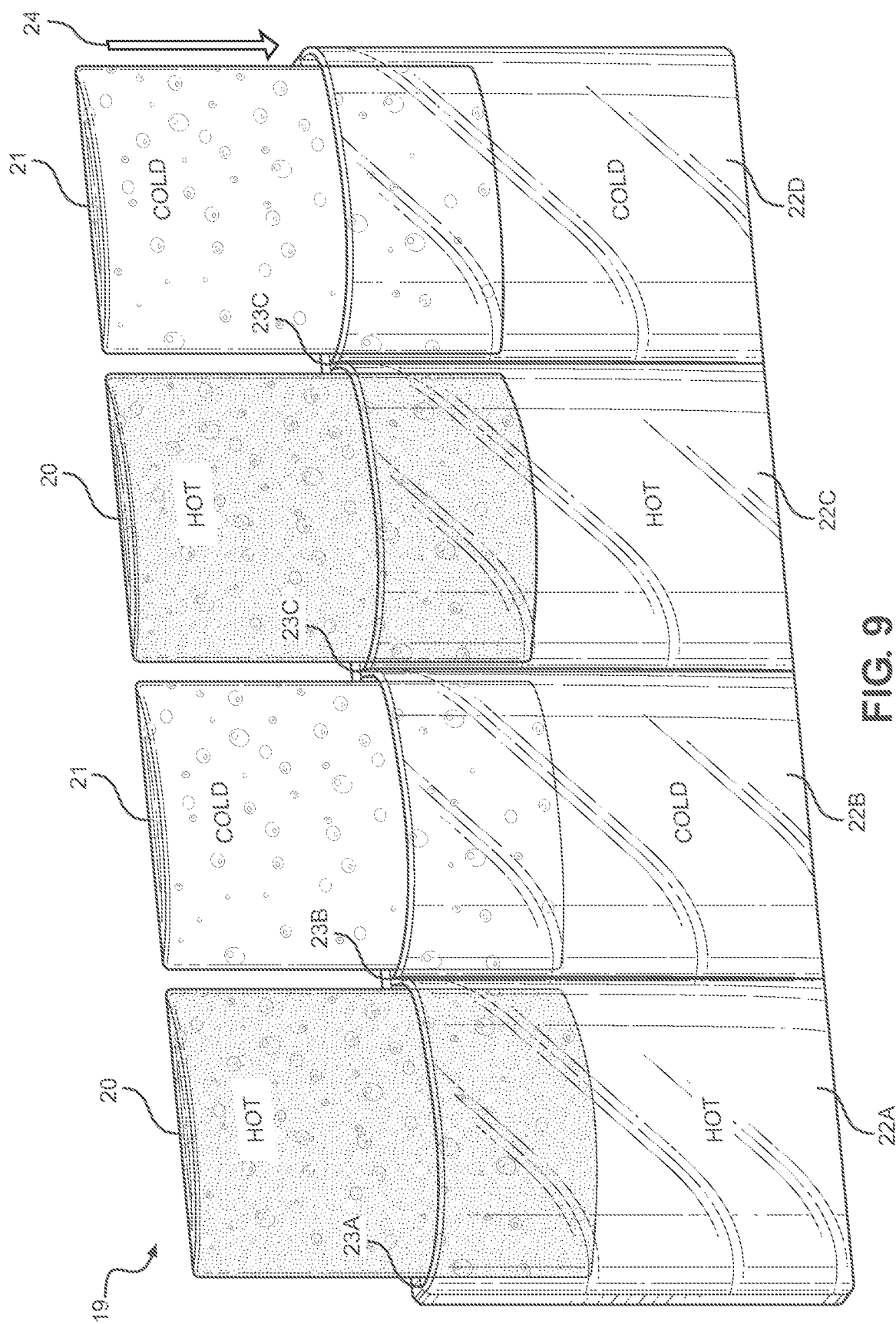
FIG. 9 is a side perspective view of an alternate embodiment of the novel therapeutic device having a rectangular shape with a plurality of pockets configured to receive alternating removable hot packs and removable cold packs evenly through the therapeutic device.

FIG. 9 is an alternate embodiment of novel therapeutic device 19 having a rectangular shape with a plurality of pockets 22A-22D each having pocket openings 23A-23D respectively. Pocket openings 23A-23D are configured to receive alternating removable hot packs 20 and removable cold packs 21 evenly through therapeutic device 19. For example, removable hot packs 20 and removable cold packs 21 slide into 24 pocket openings 23A-23D.

Figure 10:
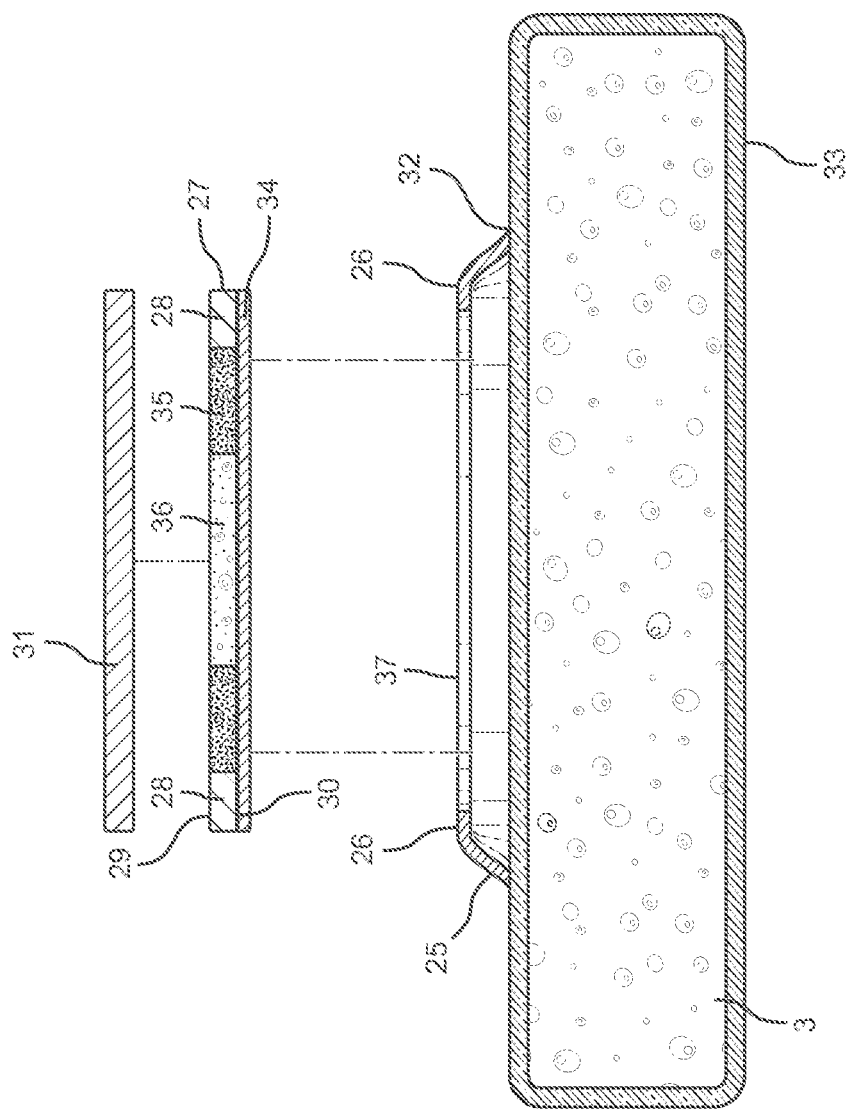
FIG. 10 is a side perspective view of an alternate embodiment of the novel removable second pack with a retaining structure receiving a removable layer of material having at least one substance.

FIG. 10 illustrates an alternate embodiment in which removable hot or cold pack 3 has a first side 32 located opposite second side 33. Layer of material 27 includes any material such as an insert, a patch, a disc, or a pad that may be saturated with at least one substance 35 and 36. A substance includes any medication, oil, cream, or combination of the aforementioned. Layer of material 27 has first side 29 located opposite second side 30. First side 29 of layer of material 27 can have barrier member 31. Barrier member 31 is any material such as wax paper, paper, plastic, a sticker, foil, or cardboard that overlays substances 35 and 36. Barrier member 31 serves the purpose of overlaying and covering substances 35 and 36 so these substances do not evaporate, become dried out, become contaminated, or become exposed when not in use. The barrier element 31 is removed from layer of material 27 during use so substances 35 and 36 are exposed during use. First side 29 of layer of material 27 is configured to be covered by a removable barrier element 31 including, but not limited to, paper, wax paper, plastic, and/or film. Second side 30 of layer of material 27 is connected to adhesive layer 34. Adhesive layer 34 may be any material capable of retaining layer of material 27 within retaining structure 25 including but not limited to, gel, rubber, glue. It is within the scope of this invention for layer of material 27 to not shift within retaining structure 25, as the importance of at least one substance 35 and/or 36 being in alignment with window 37 is critical to the layout of the structural components of this device. Second side 30 of layer of material 27 can have adhesive layer 34 that connects to first side 32 of removable second pack 3.

Figure 12:
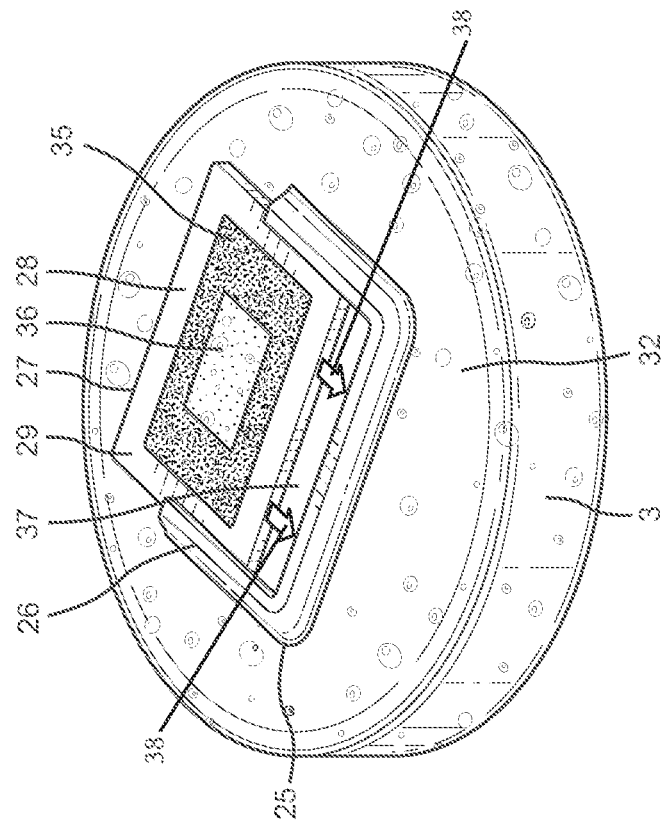
Figure 11:
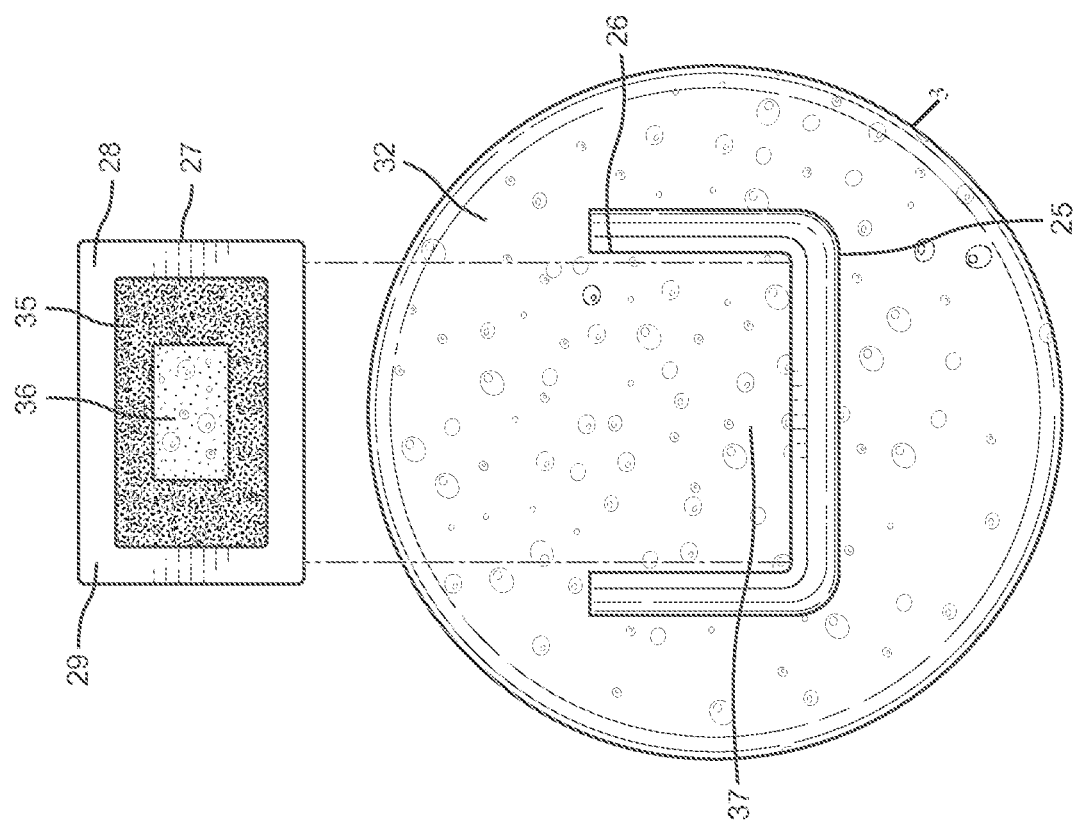
FIG. 11 is a top exploded view of the alternate embodiment of the novel removable second pack with a retaining structure receiving a removable layer of material having at least one substance; and, FIG. 12 is a perspective view of the alternate embodiment of the novel removable second pack with a retaining structure receiving a removable layer of material having at least one substance.

FIGS. 10-12 illustrate second pack 3 with retaining structure 25 connected to a layer of material 27 being a medicated pad. Second pack 3 may be a hot or cold therapeutic pack having retaining structure 25 connected to first side 32 of second pack 3. Second pack 3 has first side 32 located opposite second side 33 of second pack 3. Retaining structure 25 may be made of any material such as fabric, plastic, metal, and/or rubber capable of receiving a layer of material 27. Retaining structure 25 is configured to expose at least a portion of substance 35 and/or 36 on layer of material 27 to a user's skin during use. Layer of material 27 has first side 29 located opposite second side 30 (FIG. 10). Layer of material 27 has outer perimeter edge 28 configured to connect with flange 26 of retaining structure 25 in such a way that flange 26 directly overlays at least a portion of substance-free outer perimeter edge 28 of layer of material 27. Flange 26 is a lip that protrudes from retaining structure 25 in a direction towards the opening or window 37. Retaining structure 25 forms a pocket having an open window 37.

Referring again to FIGS. 10-12, layer of material 27 slides into 38 (FIG. 12) an opening of the retaining structure 25 and is held into place with flange 26. The retaining structure 25 may have 3 walls and may have a side opening or may have one U-shaped wall with a side opening. Flange 26 of retaining structure 25 contacts at least a portion of an outer perimeter edge 28 of layer of material 27 and exposes a substantially central portion of layer of material 27 from an opening or window 37 portion of the formed pocket. The substantially central portion of layer of material 27 can retain at least one substance 36 and/or 36. A first substance 35 and a second substance 36 are both retained on layer of material 27. It is within the scope of this current invention for the first substance 35 to fully surround the outer perimeter edge of a second substance 36. It is within the scope of this invention for first substance 35 to have an outer perimeter edge bordering the layer of material completely free of a substance. This area 28 is free of substance because it is not desirable to waste substances due to cost as this area 28 will be connected to flange 26 and not a user's skin. Also, substances should not come into contact with retaining structure 25 because the oils and/or medication may deteriorate the material over time. The substances 36 and 36 positioned on layer of material 27, when inserted into retaining structure 25, are exposed through window 37 of retaining structure 25 so they can contact a user's skin during use.

It is within the scope of this invention for layer of material 27 to provide simultaneous multiple drug delivery by topical application of a first substance 35 and a second substance 36 retained on layer of material 27 being for example, a circular absorbent portion, in which two absorbent portions deliver different medications in close proximity. For example, a first substance 35 containing menthol surrounded by a second substance 36 of camphor would result in confusion of the nervous system in such a way that a higher dose of both ingredients could be applied because camphor creates the sensation of heat while menthol creates the sensation of cold, while neither is actually delivering heat or cold. By using various combinations of active ingredients of the substance in a suitable carrier emulsion, treatment of injury or discomfort can be optimized. It is withing the scope of this invention for a carrier emulsion to include, but not be limited to, a combination of water, sodium lauryl sulfate, emulsifying wax, a preservative, and/or a carrier oil similar to the base emulsion used by pharmacists when making custom drugs. The base emulsion could be mixed with any substance including, but not limited to, topical anesthetics such as, Tetracaine, Lidocaine, or Benzocaine; topical antibiotics such as Bacitracin, Neomycin, or Polymyxin B; skin protectants such as, Dimethicone, Glycerin, or Aloe vera, and/or transdermal conductors such as, Decamethylcyclopentasiloxane, Dimethyl Sulfoxide, or Dimethyl Isosorbide.

Layer of material 27 can be partially or fully saturated with at least one or a plurality of various substances 35, 36 and may be removably inserted into the therapeutic device 1 for manipulating local blood flow, to speed healing, or to reduce discomfort faster or better than traditional methods. The primary reason for using device 1 is to achieve more precise treatment than simply applying a cold or hot compress or using a cream or lotion to alleviate discomfort, thereby, improving quality of life for the user. The substances 35 and 36 may be liquid saturating the layer of material 27, a gel, and/or a cream.

It is within the scope of this invention for layer of material 27 to provide simultaneous multiple herbal and/or homeopathic topical delivery to a user. The delivery of two different substances 35 and 36 including, but not being limited to, an herbal, a homeopathic, and/or essential oil-type product being retained on layer of material 27 can also be extended to non-drug applications. These substances include, but are not limited to, cooling essential oils such as Eucalyptus, Peppermint, or Melaleuca; calming essential oils such as, Cardamom, Chamomile, Calendula; toxin extraction such as, Bentonite, Magnesium Sulfate, or Micronized Carbon; and/or blood flow increasing resins such as, Arnica, Capsicum, Pepper Derivatives. For example, first substance 35 may include Eucalyptus Essential Oil and second substance 36 may include Capsicum Oleoresin in a carrier oil. This application would also confuse the nervous system in such a way that it would tolerate higher doses of each ingredient which would not be tolerated if applied separately. It is within the scope of this invention for substances 35 and 36 to be in close proximity of each other to allow a user to more precisely deliver treatment, to reduce healing time, and to improve quality of life. In particular, the close proximity is achieved when the first substance 35 boarders the outer perimeter edge of second substance 36.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

The invention claimed is:

1. A simultaneous thermal and cooling therapeutic device, comprising:
   said therapeutic device having a donut shape with an outer perimeter edge, said outer perimeter edge of said therapeutic device having a compartment retaining a material having a first temperature;
   said therapeutic device having a substantially central portion configured to receive a removable pack having a second temperature, said removable pack having a first side located opposite a second side;
   a layer of material, said layer of material being removably connected to said first side of said removable pack, said layer of material having a first side located opposite a second side, said layer of material having a substance-free outer perimeter, said layer of material having a first substance having an outer perimeter edge located in close proximity to a second substance having an outer perimeter edge, whereby, said first substance borders said outer perimeter edge of said second substance, said outer perimeter edge of said first substance borders said substance-free outer perimeter of said layer of material;
   said first side of said removable pack having a retaining structure configured to retain at least a portion of said layer of material, said retaining structure comprising a U-shaped wall having a flange, said retaining structure forming a pocket having an open window, said at least one flange overlaying at least a portion of said substance-free outer perimeter of said layer of material, said flange being a lip that protrudes from said retaining structure in a direction towards said open window, whereby, said first substance and said second substance are in alignment with said open window when said flange is connected to said substance-free outer perimeter of said layer of material.

2. The simultaneous thermal and cooling therapeutic device of claim 1, further comprising said outer perimeter edge of said therapeutic device retaining a thermally conductive material.

3. The simultaneous thermal and cooling therapeutic device of claim 1, further comprising said substantially central portion of said therapeutic device having a pocket, said pocket configured to retain said removable pack.

4. The simultaneous thermal and cooling therapeutic device of claim 1, further comprising said substantially central portion of said therapeutic device having a first portion of a fastener, said removable pack having a second portion of a fastener, said first portion of said fastener removably connects to said second portion of said fastener.

5. The simultaneous thermal and cooling therapeutic device of claim 1, further comprising said first substance is a topical antibiotic.

6. The simultaneous thermal and cooling therapeutic device of claim 1, further comprising said first substance being Eucalyptus Essential Oil and said second substance being Capsicum Oleoresin in a carrier oil.

7. The simultaneous thermal and cooling therapeutic device of claim 6, further comprising said first substance being menthol and said second substance being camphor.

8. The simultaneous thermal and cooling therapeutic device of claim 6, further comprising said first substance being an oil selected from the group consisting of cardamom, chamomile, and calendula.

9. The simultaneous thermal and cooling therapeutic device of claim 8, further comprising said second substance being a toxin extract selected from the group consisting of bentonite, magnesium sulfate, and micronized carbon.

10. The simultaneous thermal and cooling therapeutic device of claim 8, further comprising said second substance being a blood flow increasing resin selected from the group consisting arnica, capsicum, and pepper derivative.

11. The simultaneous thermal and cooling therapeutic device of claim 6, further comprising said first substance being an oil selected from the group consisting of eucalyptus, peppermint, and melaleuca.

12. The simultaneous thermal and cooling therapeutic device of claim 11, further comprising said second substance being a toxin extract selected from the group consisting of bentonite, magnesium sulfate, and micronized carbon.

13. The simultaneous thermal and cooling therapeutic device of claim 11, further comprising said second substance being a blood flow increasing resin selected from the group consisting of arnica, capsicum, and pepper derivative.

14. The simultaneous thermal and cooling therapeutic device of claim 6, further comprising said first substance being a topical anesthetic selected from the group consisting of tetracaine, lidocaine, and benzocaine.

15. The simultaneous thermal and cooling therapeutic device of claim 14, further comprising said second substance being a skin protectant selected from the group consisting of dimethicone, glycerin, and aloe vera.

16. The simultaneous thermal and cooling therapeutic device of claim 14, further comprising said second substance being a transdermal conductor selected from the group consisting of Decamethylcyclopentasiloxane, dimethyl sulfoxide, and dimethyl isosorbide.

\* \* \* \* \*